US012622865B2

(12) United States Patent
Vyas et al.

(10) Patent No.: US 12,622,865 B2
(45) Date of Patent: May 12, 2026

(54) ORAL CARE COMPOSITIONS AND METHODS OF USE

(71) Applicant: Colgate-Palmolive Company, New York, NY (US)

(72) Inventors: Manas Vyas, Mumbai (IN); Sandip Rege, Mumbai (IN); Ekta Makwana, Monroe, NJ (US); Manish Mandhare, Navi Mumbai (IN); Manisha Jha, Mumbai (IN); Bernal Stewart, Somerset, NJ (US); Payal Arora, Bridgewater, NJ (US); Bhagyashri Chavan, Mumbai (IN)

(73) Assignee: Colgate-Palmolive Company, New York, NY (US)

( * ) Notice: Subject to any disclaimer, the term of this patent is extended or adjusted under 35 U.S.C. 154(b) by 717 days.

(21) Appl. No.: 17/632,174

(22) PCT Filed: Dec. 2, 2021

(86) PCT No.: PCT/US2021/061603
§ 371 (c)(1),
(2) Date: Feb. 1, 2022

(87) PCT Pub. No.: WO2022/120042
PCT Pub. Date: Jun. 9, 2022

(65) Prior Publication Data
US 2022/0362138 A1 Nov. 17, 2022

(30) Foreign Application Priority Data
Dec. 2, 2020 (IN) ............................. 202011052478

(51) Int. Cl.
| | |
|---|---|
| *A61K 8/9789* | (2017.01) |
| *A61K 8/19* | (2006.01) |
| *A61K 8/21* | (2006.01) |
| *A61K 8/24* | (2006.01) |
| *A61K 8/27* | (2006.01) |
| *A61K 31/125* | (2006.01) |
| *A61K 33/10* | (2006.01) |
| *A61K 33/16* | (2006.01) |
| *A61K 33/30* | (2006.01) |
| *A61K 33/42* | (2006.01) |
| *A61K 36/27* | (2006.01) |
| *A61K 36/47* | (2006.01) |
| *A61K 36/58* | (2006.01) |
| *A61K 36/61* | (2006.01) |
| *A61Q 11/00* | (2006.01) |

(52) U.S. Cl.
CPC .............. *A61K 8/9789* (2017.08); *A61K 8/19* (2013.01); *A61K 8/21* (2013.01); *A61K 8/24* (2013.01); *A61K 8/27* (2013.01); *A61K 31/125* (2013.01); *A61K 33/10* (2013.01); *A61K 33/16* (2013.01); *A61K 33/30* (2013.01); *A61K 33/42* (2013.01); *A61K 36/27* (2013.01); *A61K 36/47* (2013.01); *A61K 36/58* (2013.01); *A61K 36/61* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 3,535,421 A | 10/1970 | Briner et al. | |
| 3,678,154 A | 7/1972 | Widder et al. | |
| 4,842,847 A | 6/1989 | Amjad | |
| 4,885,155 A | 12/1989 | Parran, Jr. et al. | |
| 6,485,710 B2 | 11/2002 | Zuckerman | |
| 6,610,277 B2 | 8/2003 | Zuckerman | |
| 9,486,396 B2 | 11/2016 | Jaracz et al. | |
| 10,058,493 B2 | 8/2018 | Manus et al. | |
| 10,342,750 B2 | 7/2019 | Prencipe et al. | |
| 10,441,517 B2 | 10/2019 | Prencipe et al. | |
| 10,617,620 B2 | 4/2020 | Prencipe et al. | |
| 10,744,077 B2 | 8/2020 | Manus et al. | |
| 11,278,477 B2 | 3/2022 | Prencipe | |
| 2004/0156920 A1* | 8/2004 | Kane ...................... | A01N 63/10 424/754 |
| 2005/0255180 A1* | 11/2005 | Tewari ................... | A61K 36/61 424/725 |
| 2006/0263825 A1* | 11/2006 | Denny ...................... | A61P 1/02 435/7.1 |

(Continued)

FOREIGN PATENT DOCUMENTS

| | | |
|---|---|---|
| CN | 106420875 | 2/2017 |
| JP | 2009263332 | 11/2009 |
| WO | 2019/045781 | 3/2019 |

OTHER PUBLICATIONS

Singh et al ("Diabetes an inducing factor for dental caries: A case control analysis in Jammu", Journal of International Society of Preventive and Community Dentistry, vol. 6(2) (2016), p. 125-9) (Year: 2016).*
Tiwari et al ("Phytochemical and Pharmacological Properties of Gymnema sylvestre: An Important Medicinal Plant", Biomedical Research International, vol. 2014, Article ID 830285 (2014), p. 1-18) (Year: 2014).*

(Continued)

*Primary Examiner* — Sin J Lee

(57) ABSTRACT

This invention relates to oral care compositions comprising herbal extracts including, e.g., *Gymnema sylvestre, Emblica officinalis, Eugenia jambolana, Azadirachta indica*, and combinations thereof and zinc salts, e.g., zinc citrate and zinc oxide. Additionally, the invention relates to methods of using and of making these compositions, e.g., method of using the oral care compositions to treat gingivitis in diabetic consumers.

16 Claims, No Drawings

(56) References Cited

U.S. PATENT DOCUMENTS

| | | |
|---|---|---|
| 2008/0102143 A1* | 5/2008 | Freis ........................ A61Q 7/02 |
| | | 424/774 |
| 2009/0202454 A1 | 8/2009 | Mello et al. |
| 2013/0071456 A1 | 3/2013 | Fruge et al. |
| 2015/0313813 A1 | 11/2015 | Rege et al. |
| 2017/0322210 A1 | 11/2017 | Stettler et al. |
| 2017/0367945 A1 | 12/2017 | Sirdesai et al. |
| 2018/0015016 A1 | 1/2018 | Huang et al. |
| 2019/0038531 A1 | 2/2019 | Rege et al. |
| 2019/0365833 A1 | 12/2019 | Gotz et al. |
| 2020/0009031 A1 | 1/2020 | Prencipe et al. |
| 2020/0337959 A1 | 10/2020 | Manus et al. |

OTHER PUBLICATIONS

Chaudhry et al ("Effect of Eugenia Jambolana on No. of Inflammatory Cells in Gingivitis in Albino Rats", Professional Medical Journal, vol. 26(11) (2019), p. 2021-2032) (Year: 2019).*
Agasthiyar, 1992, "Kundiakkarathirku Karkam-ii", Balavakadam: 268-274.
Bhavamisra, 2000, "Triphaladikvathah", Bhavaprakasa—Edited & translated by Brahmasankara Misra, part II, Edn. 7:706
Mohammad Najmul Ghani Khan, 1911, "Sanoon Chob-e-Jamun", Khazaain-al-Advia, vol II: 242.
Mohammad Najmul Ghani Khan, 1926, "Joshaanda Bara-e—Amraaz-e—Masoodah", Khazaain-al-Advia, vol. III: 994.
Susruta, 2001, "Dhatakyadipratisaranam", Susruta Samhita—Edited & translated by P.V Sharma, vol. III:9-10.
Anonymous, 2003, "Paradontosis Prevention Toothpaste", Mintel Database GNPD AN:194763.
Anonymous, 2017, "Complete Care Toothpaste with Simply Cinnamon Flavour", Mintel Database GNPD AN: 5008641.
Anonymous, 2019, "Advanced Dental Cream", Mintel Database GNPD AN: 6300577.
Anonymous, 2020, "Aloe Vera Toothpaste with Mint-Clove", Mintel Database GNPD AN:7154229.
International Search Report and the Written Opinion of the International Searching Authority issued in International Application PCT/US2021/061603 mailed Apr. 7, 2022.
1990, "Gudamara Arka", Rasatantrasarah Evam Siddhaprayogasamgrahah, part I, pp. 778-779.
Agasthiyar, 1933, "Kundiakkarathirku Karkam—ii", Balavakadam, pp. 268-274.
Mohammad Najmul Ghani Khan, 1928, "Dawa-e-Ziabetus", Qaraabaadeen Najm-al-Ghani, second edition, pp. 239.
Susruta, 2001, "Dhatakyadipratisaranam", Susruta Samhita, Edited and Translated by P.V. Sharma, vol. III, Edn. Ist, pp. 9-10.
Wang, Muxiang, (1997) "Modern Chinese Medicine Pharmacology," Tianjin Science and Technology Press, published Jan. 31, 1997, pp. 1024-1025.
Preshaw et al., "Periodontitis and diabetes: a two-way relationship," Diabetologia, Jan. 2012, 55(1):21-31.
Silness et al., Periodontal Disease in Pregnancy. II. Correlation Between Oral Hygiene and Periodontal Condition, Acta Odontol. Scand. Feb. 1964, 22:121-35.

* cited by examiner

ORAL CARE COMPOSITIONS AND METHODS OF USE

This invention relates to oral care compositions comprising herbal extracts including, e.g., *Gymnema sylvestre*, or *Emblica officinalis*, or *Eugenia jambolana*, or *Azadirachta indica*, and combinations thereof and zinc salts, e.g., zinc citrate and zinc oxide. Additionally, the invention relates to methods of using and of making these compositions, e.g., method of using the oral care compositions to treat gingivitis in diabetic consumers.

BACKGROUND

Gingivitis is an inflammation of gums. If not treated at the early stage it leads to a more severe condition called Periodontitis. Gingivitis occurs in a significant proportion of adults. One of the major risk factors for gingivitis is diabetes. While the mechanisms of action are not completely understood, previous research has demonstrated that there may be a relationship between the degree of hyperglycaemia and severity of periodontitis. There is some understanding in the field that diabetes can have deleterious downstream effects on immune dysfunction, cellular stress and cytokine imbalance (e.g., inflammation). Some of the various inflammatory cytokines that can be increased with the diabetic condition can include, e.g., TNF-alpha, IL-6, and IL-1β.

Researchers in the field have posited that diabetes increases the risk for periodontal inflammation then negatively affecting glycaemic control. However, some have indicated that treatment of periodontitis is associated with $HbA_{1c}$ reductions of approximately 0.4%. See e.g., Preshaw, P. et al., Diabetologia. 2012 January; 55(1): 21-31. Accordingly, diabetic individuals can have specific treatment needs that pertain to oral health maintenance.

Accordingly, there is a current need for a toothpaste for individuals that have gingivitis, at risk for periodontal disease, diabetes, or that are at risk for diabetes.

BRIEF SUMMARY

It is believed that the current formulations offer the advantage of treatments that can be beneficial to individuals that have gingivitis, or at risk for gingivitis, in diabetic consumers, or those that are at risk for diabetes, and/or inflammation or gum bleeding in the oral cavity. In one aspect, oral care compositions of the described herein are generally effective for treating inflammation, bleeding and gingivitis in the oral cavity (e.g., specifically acting upon the gingival tissue). In one aspect, the composition is specifically useful to treat inflammation in the oral cavity that is mediated by IL-1β, e.g., in diabetic individuals that have IL-1β mediated inflammation.

In one aspect, the application contemplates that a formulation with an herbal extract source comprising, e.g., *Gymnema sylvestre, Emblica officinalis, Eugenia jambolana, Azadirachta indica* along with zinc salts (e.g., zinc citrate and zinc oxide) can be useful to treat gingivitis, individuals at risk for gingivitis in diabetic consumers, or individuals at risk for diabetes. In one aspect, the inventors have found that gurmar raw material has in-vitro efficacy as an anti-inflammatory compound. In another aspect, it was determined that in toothpastes with *gymnema sylvestre* could reduce inflammation and gum bleeding significantly in clinical studies, as compared to control samples that did not contain any *gymnema sylvestre*.

In one aspect the invention is an oral care composition (Composition 1.0) comprising:

a. an effective amount of a zinc ion source (e.g., a zinc ion source comprising zinc citrate and zinc oxide)

b. A fluoride source (e.g., sodium monofluorophosphate); and c. An herbal extract source comprising *Gymnema sylvestre*, or *Emblica officinalis*, or *Eugenia jambolana*, or *Azadirachta indica*, and combinations thereof.

For example, the invention contemplates any of the following compositions (unless otherwise indicated, values are given as percentage of the overall weight of the composition)

1.1 Composition 1.0 further comprising a polyphosphate.

1.2 Any of the preceding compositions wherein the zinc ion source comprises zinc citrate and zinc oxide, wherein the ratio of the amount of zinc oxide (e.g., wt. %) to zinc citrate (e.g., wt %) is from 1.5:1 to 4.5:1 (e.g., 2:1, 2.5:1, 3:1, 3.5:1, or 4:1).

1.3 Any of the preceding compositions comprising zinc citrate and zinc oxide, wherein the zinc citrate is in an amount of from 0.25 to 1 wt % (e.g., 0.5 wt. %) and zinc oxide may be present in an amount of from 0.75 to 1.25 wt % (e.g., 1.0 wt. %) based on the weight of the oral care composition.

1.4 Any of the preceding compositions comprising zinc oxide and zinc citrate wherein the zinc citrate is about 0.5 wt % relative to the total weight of the oral care composition (e.g., zinc citrate trihydrate).

1.5 Any of the preceding compositions comprising zinc oxide and zinc citrate wherein the zinc oxide is about 1.0 wt % relative to the total weight of the oral care composition.

1.6 Any of the preceding compositions comprising zinc oxide and zinc citrate where the zinc citrate is about 0.5 wt % and the zinc oxide is about 1.0 wt %, relative to the total weight of the oral care composition.

1.7 Any of the preceding compositions wherein the fluoride source comprises a fluoride source selected from: stannous fluoride, sodium fluoride, potassium fluoride, sodium monofluorophosphate, sodium fluoro silicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.8 Any of the preceding compositions wherein the fluoride source is a fluorophosphate.

1.9 Any of the preceding compositions wherein the fluoride source is sodium monofluorophosphate.

1.10 Any of the preceding compositions wherein the fluoride source is sodium fluoride.

1.11 Any of the preceding compositions wherein the fluoride source is a fluoride salt present in an amount of 0.1 wt. % to 2 wt. % (0.1 wt %-0.6 wt. %) relative to the total composition weight (e.g., sodium fluoride (e.g., about 0.3 wt. %) or sodium monofluorophosphate).

1.12 Any of the preceding compositions wherein the fluoride source is a soluble fluoride salt which provides fluoride ion in an amount of from 50 to 25,000 ppm (e.g., 750-2000 ppm, e.g., 1000-1500 ppm, e.g., about 1000 ppm, e.g., about 1450 ppm)

1.13 Any of the preceding compositions wherein the fluoride source is sodium fluoride which provides fluoride in an amount from 750-2000 ppm (e.g., about 1450 ppm)

1.14 Any of the preceding compositions wherein the fluoride source is selected from sodium fluoride and sodium monofluorophosphate and which provides fluoride in an amount from 1000 ppm-1500 ppm.

1.15 Any of the preceding compositions wherein the fluoride source is sodium fluoride or sodium monofluorophosphate and which provides fluoride in an amount of about 1450 ppm.

1.16 Any of the preceding compositions wherein the fluoride source comprises sodium monofluorophosphate. (e.g., from 0.5%-1.0% by wt.) (e.g., about 0.76% by wt.)

1.17 Any of the preceding compositions, wherein the composition comprises a copolymer.

1.18 The composition of 1.18, wherein the copolymer is a PVM/MA copolymer.

1.19 The composition of 1.19, wherein the PVM/MA copolymer comprises a 1:4 to 4:1 copolymer of maleic anhydride or acid with a further polymerizable ethylenically unsaturated monomer; for example 1:4 to 4:1, e.g., about 1:1.

1.20 Any of the preceding compositions, wherein the further polymerizable ethylenically unsaturated monomer comprises methyl vinyl ether (methoxyethylene).

1.21 Any of the preceding compositions, wherein the PVM/MA copolymer comprises a copolymer of methyl vinyl ether/maleic anhydride, wherein the anhydride is hydrolyzed following copolymerization to provide the corresponding acid.

1.22 Any of the preceding compositions, wherein the PVM/MA copolymer comprises a GANTREZ® polymer (e.g., GANTREZ® S-97 polymer)

1.23 Any of the preceding compositions wherein the pH is between 7.5 and 10.5. e.g., about 7.5 or about 8.0.

1.24 Any of the preceding compositions further comprising a fluoride ion source.

1.25 The composition of 1.24, wherein the fluoride ion source is selected from the group consisting of stannous fluoride, sodium fluoride, potassium fluoride, sodium monofluorophosphate, sodium fluorosilicate, ammonium fluorosilicate, amine fluoride, ammonium fluoride, and combinations thereof.

1.26 Any of the preceding compositions wherein the polyphosphate is sodium tripolyphosphate (STPP).

1.27 The composition of 1.26, wherein the sodium tripolyphosphate is from 0.5-5.0 wt % (e.g., about 3.0 wt %).

1.28 Any of the preceding compositions further comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, disodium hydrogenorthophoshpate, monosodium phosphate, pentapotassium triphosphate and mixtures of any of two or more of these, e.g., in an amount of 1-20%, e.g., 2-8%, e.g., ca. 5%>, by weight of the composition.

1.29 Any of the preceding compositions further comprising an abrasive or particulate (e.g., silica) (e.g., calcium carbonate)

1.30 The composition of 1.29, wherein the abrasive or particulate is selected from sodium bicarbonate, calcium phosphate (e.g., dicalcium phosphate dihydrate), calcium sulfate, precipitated calcium carbonate, calcium pyrophosphate, silica (e.g., hydrated silica), iron oxide, aluminum oxide, perlite, plastic particles, e.g., polyethylene, and combinations thereof.

1.31 The composition of 1.30, wherein the abrasive is calcium carbonate (e.g., precipitated calcium carbonate, natural calcium carbonate, or a mixture thereof)

1.32 Any of the preceding compositions wherein the silica is synthetic amorphous silica. (e.g., 1%-25% by wt.) (e.g., 8%-25% by wt.) (e.g., about 12% by wt.)

1.33 Any of the preceding composition wherein the silica abrasives are silica gels or precipitated amorphous silicas, e.g., silicas having an average particle size ranging from 2.5 microns to 12 microns.

1.34 Any of the preceding compositions further comprising a small particle silica having a median particle size (d50) of 1-5 microns (e.g., 3-4 microns) (e.g., about 5 wt. % Sorbosil AC43 from Ineos Silicas, Warrington, United Kingdom).

1.35 Any of the preceding compositions wherein 20-30 wt % of the total silica in the composition is small particle silica (e.g., having a median particle size (d50) of 3-4 microns) and wherein the small particle silica is about 5 wt. % of the oral care composition.

1.36 Any of the preceding compositions comprising silica wherein the silica is used as a thickening agent, e.g., particle silica.

1.37 Any of the preceding compositions wherein the abrasive or particulate comprises calcium carbonate (e.g., precipitated calcium carbonate).

1.38 The composition of 1.37, wherein the calcium carbonate is in an amount from 20-50% by wt. relative to the total composition (e.g., about 40% by wt.)

1.39 Any of the preceding compositions further comprising an anionic surfactant, wherein the nonionic surfactant is in an amount of from 0.5-5% by wt., e.g., 1-2% by weight, selected from water-soluble salts of higher fatty acid monoglyceride monosulfates, (e.g., sodium N-methyl N-cocoyl taurate), sodium cocomo-glyceride sulfate; higher alkyl sulfates, (e.g., sodium lauryl sulfate); higher alkyl-ether sulfates (e.g., of formula $CH_3(CH_2)_mCH_2(OCH_2CH_2)_nOSO_{3X}$, wherein m is 6-16, e.g., 10, n is 1-6, e.g., 2, 3 or 4, and X is Na) or (e.g., sodium laureth-2 sulfate $(CH_3(CH_2)_{10}CH_2(OCH_2CH_2)_2OSO_3Na)$; higher alkyl aryl sulfonates (e.g., sodium dodecyl benzene sulfonate, sodium lauryl benzene sulfonate); higher alkyl sulfoacetates (e.g., sodium lauryl sulfoacetate; dodecyl sodium sulfoacetate), higher fatty acid esters of 1,2 dihydroxy propane sulfonate, sulfocolaurate (e.g., N-2-ethyl laurate potassium sulfoacetamide) and sodium lauryl sarcosinate, and mixtures thereof.

1.40 Any of the preceding compositions, wherein the anionic surfactant is sodium lauryl sulfate (from 1.0%-7.0% by wt. relative to the total wt. % of the composition)

1.41 Any of the preceding compositions further comprising glycerin, wherein the glycerin is in a total amount of 20-50% (e.g., about 41% by wt.).

1.42 Any of the preceding compositions, wherein the ratio of the amount of zinc oxide (e.g., wt. %) to zinc citrate (e.g., wt %) is from 1.5:1 to 4.5:1 (e.g., 2:1, 2.5:1, 3:1, 3.5:1, or 4:1).

1.43 Any of the preceding compositions, wherein the zinc citrate is in an amount of from 0.25 to 1 wt % (e.g., 0.5 wt. %) and zinc oxide may be present in an amount of from 0.75 to 1.25 wt % (e.g., 1.0 wt. %) based on the weight of the oral care composition.

1.44 Any of the preceding compositions wherein the zinc citrate is about 0.5 wt %.

1.45 Any of the preceding compositions wherein the zinc oxide is about 1.0 wt %.

1.46 Any of the preceding compositions where the zinc citrate is about 0.5 wt %, and the zinc oxide is about 1.0 wt %, where the wt. % is relative to the total weight of the oral care composition 1.47 Any of the preceding compositions comprising polymer films.

1.48 Any of the preceding compositions comprising flavoring, fragrance and/or coloring.

1.49 Any of the preceding compositions, wherein the composition comprises a thickening agent selected from the group consisting of carboxyvinyl polymers, carrageenan, xanthan, hydroxyethyl cellulose and water soluble salts of cellulose ethers (e.g., sodium carboxymethyl cellulose and sodium carboxymethyl hydroxyethyl cellulose).

1.50 Any of the preceding compositions, wherein the compositions comprises sodium carboxymethyl cellulose (e.g., from 0.1 wt. %-2.5 wt. %) (e.g., about 0.2% by wt.).

1.51 Any of the preceding compositions comprising from 5%— 40%, e.g., 10%-35%, e.g., about 10, about 12%, about 15%, about 25%, about 30%, and about 35% water, where the wt. % is relative to the total weight of the oral care composition.

1.52 Any of the preceding compositions comprising an additional antibacterial agent selected from halogenated diphenyl ether (e.g. triclosan), herbal extracts and essential oils (e.g., rosemary extract, tea extract, *magnolia* extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, Zinc Chloride, Zinc Lactate, Zinc Sulfate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

1.53 Any of the preceding compositions comprising an antioxidant, e.g., selected from the group consisting of Co-enzyme Q10, PQQ, Vitamin C, Vitamin E, Vitamin A, BHT, anethole-dithiothione, and mixtures thereof.

1.54 Any of the preceding compositions comprising a whitening agent.

1.55 The composition of 1.54, wherein the whitening agent is titanium dioxide.

1.56 Any of the preceding compositions comprising a whitening agent selected from a whitening active selected from the group consisting of peroxides, metal chlorites, perborates, percarbonates, peroxyacids, hypochlorites, and combinations thereof.

1.57 Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.

1.58 Any of the preceding compositions further comprising an agent that interferes with or prevents bacterial attachment, e.g., ELA or chitosan.

1.59 Any of the preceding compositions further a buffer system; (e.g., wherein the buffer comprises trisodium citrate and citric acid).

1.60 Any of the preceding compositions, wherein the composition comprises an aqueous buffer system, for example, wherein the buffer system comprises an organic acid and an alkali metal salt thereof, e.g., wherein the organic acid is citric acid and the salt is a mono-, di- and/or tri-alkali metal citrate salt, e.g., mono-, di- and/or tri-lithium, sodium, potassium, or cesium citrate salt, and citric acid. For example, where the composition comprises 1-10% by weight organic acid salt and 0.1-5% by weight organic acid.

1.61 Composition of 1.60, wherein the buffer system comprises a citrate buffer, wherein the citrate buffer comprises tri-sodium citrate and citric acid (e.g., 1 to 10% by weight of the composition), for example, wherein the molar ratio of mono-, di- and/or tri-sodium citrate and citric acid is 1.5 to 5, (e.g., 2 to 4). The buffer system may be present, by weight, in an amount that is greater than the amount, by weight, of the source of stannous ions.

1.62 Any of the preceding compositions wherein the herbal extract source comprises one or more selected from the group consisting of: amla extract, honey extract, almond extract, aloe vera extract, marietta extract, ginger extract, fenugreek, neem seed oil, sesame oil, cinnamon leaf oil, clove oil, thyme oil, *eucalyptus* oil, eugenol, menthol, babool, *Eugenia jambolana* extract (e.g., seed dry extract), *melia azadirachta* (e.g., seed oil), *Gymnema sylvestre*, camphor, and combinations thereof.

1.63 Any of the preceding compositions wherein the herbal extract comprises one or more selected from: *Gymnema sylvestre*, or *Eugenia jambolana* extract (e.g., seed dry extract), or *melia azadirachta* (e.g., seed oil), or amla extract, and combinations thereof.

1.64 Any of the preceding compositions comprising *gymnema sylvestre* extract in an amount from 0.1% to 0.5% by wt. of the total composition (e.g., about 0.3% by wt.).

1.65 Any of Composition 1.0-1.64, wherein the composition comprises:

a. From 0.5%-1.5% zinc oxide (e.g., about 1.0% by wt.)

b. From 0.25%-0.75% zinc citrate (e.g., about 0.5% by wt)

c. From 0.5%-1.0% by wt of sodium monofluorophosphate (e.g., about 0.76% by wt); and d. From 0.2%-0.5% (e.g., about 0.4% by wt.) of a combination of *gymnema sylvestre* extract, *Eugenia jambolana* extract (e.g., seed dry extract), *melia azadirachta* (e.g., seed oil), and amla extract.

where the weights of the ingredients are relative to the total weight of the oral care composition

1.66 Any of Composition 1.0-1.64, wherein the composition comprises:
a. From 0.5%-1.5% zinc oxide (e.g., about 1.0% by wt.)
b. From 0.25%-0.75% zinc citrate (e.g., about 0.5% by wt)
c. From 0.5%-1.0% by wt of sodium monofluorophosphate (e.g., about 0.76% by wt); and
d. From 0.2%-0.5% of *gymnema sylvestre* extract (e.g., about 0.3% by wt.)
where the weights of the ingredients are relative to the total weight of the oral care composition
1.67 Any of the preceding compositions effective upon application to the oral cavity, e.g., by rinsing, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit malodor, (vi) promote healing of sores or cuts in the mouth, (vii) reduce levels of acid producing bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity (xiv) reduce erosion, (xv) prevents stains and/or whiten teeth, (xvi) immunize the teeth against cariogenic bacteria; and/or (xvii) promote systemic health, including cardiovascular health, e.g., by reducing potential for systemic infection via the oral tissues.
1.68 Any of the preceding oral compositions, wherein the oral composition may be any of the following oral compositions selected from the group consisting of: a toothpaste or a dentifrice, a mouthwash or a mouth rinse, a topical oral gel, a denture cleanser, a coated or impregnated immediate or delayed release oral adhesive strip or patch, and a coated or impregnated oral wipe or swab.
1.69 Any of the preceding compositions, where the only source of zinc is zinc oxide and zinc citrate.
1.70 Any of the preceding compositions, where the only source of fluoride is sodium monofluorophosphate.
1.71 Any of the preceding compositions, wherein the herbal extract source comprises *Gymnema sylvestre*, and further comprises one or more of the following: *Eugenia jambolana* extract (e.g., dry seed extract of *Eugenia jambolana*), *melia azadirachta* (e.g., seed oil of *melia azadirachta*), Amla extract, and combinations thereof.
1.72 Any of the preceding compositions further comprising nitric acid or a water-soluble nitrate salt (e.g., potassium nitrate) (e.g., wherein the potassium nitrate operates as a stabilizing agent).
1.73 The composition of 1.72, wherein the water-soluble nitrate salt is selected from an alkali or alkaline earth metal nitrate, or zinc nitrate, silver nitrate, or ammonium nitrate.
1.74 The composition of 1.72 or 1.73, wherein the water-soluble nitrate salt is an alkali metal nitrate salt or an alkaline earth metal nitrate salt.
1.75 The composition of 1.74, wherein the nitrate salt is selected from lithium nitrate, sodium nitrate, potassium nitrate, magnesium nitrate, and calcium nitrate.

1.76 The composition of 1.75, wherein the nitrate salt is potassium nitrate (e.g., wherein potassium nitrate operates a stabilizing agent).
1.77 A composition obtained or obtainable by combining the ingredients as set forth in any of the preceding compositions.
1.78 Any of the preceding oral care compositions, wherein the composition is a dentifrice.
1.79 Any the preceding oral care compositions, wherein the composition may be any of the following selected from: a toothpaste, transparent paste, gel, mouth rinse, mouth spray, oil-based mouthwash format, and chewing gum.
1.80 Any of the preceding oral care compositions, wherein the composition demonstrates at least a 50% reduction in gum bleeding, relative to a control, wherein the reduction is measured by the Loe-Silness Gingival Index.
1.81 Any of the preceding oral care compositions, wherein the composition demonstrates at least a 30% reduction in inflammation, relative to a control, wherein the reduction is measured by the Ayurveda Visual Analog Scale.
1.82 Any of the preceding oral care compositions, wherein the composition demonstrates at least a 25% reduction in gum bleeding, relative to a control, wherein the reduction is measured by the Ayurveda Visual Analog Scale.
1.83 Any of the preceding oral care compositions, wherein the composition demonstrates at least a 35% reduction in gum sponginess, relative to a control, wherein the reduction is measured by the Ayurveda Visual Analog Scale.
1.84 Any of the preceding oral care compositions, wherein the composition is administered in an amount effective to reduce IL-1$\beta$ mediated inflammation.
1.85 Any of the preceding oral care compositions, wherein the zinc ion source comprises one or more zinc salts selected from the group consisting of: zinc chloride, zinc lactate, zinc citrate, zinc oxide, zinc sulfate, zinc gluconate, zinc phosphate and combinations thereof.
A composition for use as set for in any of the preceding compositions of Composition 1.0 et seq.
In another embodiment, the invention encompasses a method to improve oral health comprising applying an effective amount of the oral composition of any of the embodiments (e.g., any of Compositions 1.0 et seq) set forth above to the oral cavity of a subject in need thereof, e.g., a method to
i. reduce or inhibit formation of dental caries,
ii. reduce levels of acid producing bacteria,
iii. inhibit microbial bio film formation in the oral cavity,
iv. reduce plaque accumulation,
v. immunize (or protect) the teeth against cariogenic bacteria and their effects, and/or
vi. clean the teeth and oral cavity.
The invention further comprises the use of sodium bicarbonate, sodium methyl cocoyl taurate (tauranol), MIT, and benzyl alcohol and combinations thereof in the manufacture of a Composition of the Invention, e.g., for use in any of the indications set forth in the above method of Composition 1.0, et seq.
In another aspect, any of Composition 1.0 et seq, can be used in a method to treat inflammation, tissue damage, and/or immunomodulatory dysfunction in the oral cavity.

In another aspect, any of Composition 1.0 et seq, can be used in a method (Method 2.0). In one aspect, Method 2.0 is a method for treating or reducing gingivitis in a subject in need thereof, wherein the method comprises administering an oral care composition comprising:

a. an effective amount of a zinc ion source (e.g., a zinc ion source comprising zinc citrate and zinc oxide)

b. A fluoride source (e.g., sodium monofluorophosphate); and c. An herbal extract source comprising *Gymnema sylvestre*, or *Emblica officinalis*, or *Eugenia jambolana*, or *Azadirachta indica*, and combinations thereof.

For example, the invention contemplates any of the following compositions (unless otherwise indicated, values are given as percentage of the overall weight of the composition)

2.1 The composition of Method 2.0, wherein the ratio of the amount of zinc oxide (e.g., wt. %) to zinc citrate (e.g., wt %) is from 1.5:1 to 4.5:1 (e.g., 2:1, 2.5:1, 3:1, 3.5:1, or 4:1).

2.2 Any of the preceding methods wherein the composition comprises zinc citrate and zinc oxide, wherein the zinc citrate is in an amount of from 0.25 to 1 wt % (e.g., 0.5 wt. %) and zinc oxide may be present in an amount of from 0.75 to 1.25 wt % (e.g., 1.0 wt. %) based on the weight of the oral care composition.

2.3 Any of the preceding methods wherein the zinc citrate is about 0.5 wt % (e.g., zinc citrate trihydrate).

2.4 Any of the preceding methods wherein the zinc oxide is about 1.0 wt %.

2.5 Any of the preceding methods where the zinc citrate is about 0.5 wt % and the zinc oxide is about 1.0 wt %.

2.6 Any of the preceding methods, wherein the herbal extract source comprises one or more herbal extract(s) selected from the group consisting of: *Gymnema sylvestre*, amla extract, honey extract, almond extract, aloe vera extract, marietta extract, ginger extract, fenugreek, neem seed oil, sesame oil, cinnamon leaf oil, clove oil, thyme oil, mint oil, *eucalyptus* oil, eugenol, menthol, babool, *Eugenia jambolana* extract (e.g., seed dry extract), *melia azadirachta* or *azadirachta* indica (e.g., seed oil), camphor and combinations thereof.

2.7 The preceding method, wherein the herbal extract comprises one or more selected from, *Gymnema sylvestre, Eugenia jambolana* extract (e.g., seed dry extract), *melia azadirachta* (e.g., seed oil), amla extract, and combinations thereof.

2.8 Any of the preceding methods, wherein the herbal extract source comprises *gymnema sylvestre* extract in the amount from 0.1% by wt. to 0.5% by wt. of the total composition (e.g., about 0.3% by wt.).

2.9 Any of the preceding methods wherein the subject in need thereof is at risk for periodontitis.

2.10 The preceding method, wherein the subject is at risk because the subject is diabetic or has been diagnosed with diabetes.

2.11 Any of the preceding methods, wherein the subject suffers from hyperglycemia or is a risk for periodontitis because of hyperglycemia (e.g., pre-diabetic).

2.12 Any of the preceding methods, wherein the oral care composition is administered to the subject in need thereof to treat IL-1f3 mediated inflammation.

2.13 Any of the preceding methods, wherein the subject in need thereof has localized hyperglycemia in the oral cavity.

2.14 Any of the preceding methods, wherein the subject in need thereof has gum bleeding, gum redness, or gum soreness.

2.15 The method of 2.14, wherein the subject is diabetic (e.g., Type 2 diabetes) or at risk of diabetes.

DETAILED DESCRIPTION

As used herein, an "oral care composition" refers to a composition for which the intended use includes oral care, oral hygiene, and/or oral appearance, or for which the intended method of use comprises administration to the oral cavity, and refers to compositions that are palatable and safe for topical administration to the oral cavity, and for providing a benefit to the teeth and/or oral cavity. The term "oral care composition" thus specifically excludes compositions which are highly toxic, unpalatable, or otherwise unsuitable for administration to the oral cavity. In some embodiments, an oral care composition is not intentionally swallowed, but is rather retained in the oral cavity for a time sufficient to affect the intended utility. The oral care compositions as disclosed herein may be used in nonhuman mammals such as companion animals (e.g., dogs and cats), as well as by humans. In some embodiments, the oral care compositions as disclosed herein are used by humans. Oral care compositions include, for example, dentifrice and mouthwash. In some embodiments, the disclosure provides toothpaste or mouthwash formulations.

As used herein, "orally acceptable" refers to a material that is safe and palatable at the relevant concentrations for use in an oral care formulation, such as a mouthwash or dentifrice.

As used herein, "orally acceptable carrier" refers to any vehicle useful in formulating the oral care compositions disclosed herein. The orally acceptable carrier is not harmful to a mammal in amounts disclosed herein when retained in the mouth, without swallowing, for a period sufficient to permit effective contact with a dental surface as required herein. In general, the orally acceptable carrier is not harmful even if unintentionally swallowed. Suitable orally acceptable carriers include, for example, one or more of the following: water, a thickener, a buffer, a humectant, a surfactant, an abrasive, a sweetener, a flavorant, a pigment, a dye, an anti-caries agent, an anti-bacterial, a whitening agent, a desensitizing agent, a vitamin, a preservative, an enzyme, and mixtures thereof.

As used herein, the term "dentifrice" means paste, gel, or liquid formulations unless otherwise specified. The dentifrice composition can be in any desired form such as deep striped, surface striped, multi-layered, having the gel surrounding the paste, or any combination thereof. Alternatively, the oral composition may be dual phase dispensed from a separated compartment dispenser.

As used herein, unless otherwise indicated, the term "effective amount" means the quantity of an ingredient or material required to provide an adequate benefit or improvement in the oral cavity. In one aspect, the "effective amount" of a zinc ion source is the amount of the zinc ion source required to deliver zinc ions to the gums or enamel so as to have a beneficial effect in the oral cavity (e.g., relative to control).

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As is usual in the art, the compositions described herein are sometimes described in terms of their ingredients, notwithstanding that the ingredients may disassociate, associate or react in the formulation. Ions, for example, are commonly provided to a formulation in the form of a salt, which may dissolve and dissociate in aqueous solution. It is understood that the invention encompasses both the mixture of described ingredients and the product thus obtained.

As used herein, "gymnerna *sylvestre*" refers to a perennial woody vine native to tropical Asia. China, the Arabian Peninsula, Africa, and Australia, and can also include extracts thereof. It, has been used in Ayurvedic medicine. Common names include *gymnema*, Australian cowplant, and Peripioca of the woods, and the Hindi term "gurmar". The terms "gurmar", "gudmar" and "gymnerna *sylvestre*" are used herein interchangeably.

As used herein, the terms "amla" and "*Emblica officinalis*" are used interchangeably.

Fluoride Ion Source

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., each of which are incorporated herein by reference. Representative fluoride ion sources used with the present invention (e.g., Composition 1.0 et seq.) include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. Where the formulation comprises calcium salts, the fluoride salts are preferably salts wherein the fluoride is covalently bound to another atom, e.g., as in sodium monofluorophosphate, rather than merely ionically bound, e.g., as in sodium fluoride.

Surfactants

The invention may in some embodiments contain anionic surfactants, e.g., any of Composition 1.0, et seq., for example, water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomo-glyceride sulfate; higher alkyl sulfates, such as sodium lauryl sulfate; higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or, for example sodium laureth-2 sulfate $(CH_3(CH_2)_{10}CH_2(OCH_2CH_2)_2OSO_3Na)$; higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. By "higher alkyl" is meant, e.g., C6-30 alkyl. In particular embodiments, the anionic surfactant (where present) is selected from sodium lauryl sulfate and sodium ether lauryl sulfate. When present, the anionic surfactant is present in an amount which is effective, e.g., >0.001% by weight of the formulation, but not at a concentration which would be irritating to the oral tissue, e.g., 1%, and optimal concentrations depend on the particular formulation and the particular surfactant. In one embodiment, the anionic surfactant is present at from 0.03% to 5% by weight, e.g., about 1.75% by wt.

In another embodiment, cationic surfactants useful in the present invention can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants of the disclosure, e.g., any of Composition 1.0, et seq., that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In a particular embodiment, the composition of the invention comprises a nonionic surfactant selected from poloxamers (e.g., poloxamer 407), polysorbates (e.g., polysorbate 20), polyoxyl hydrogenated castor oils (e.g., polyoxyl 40 hydrogenated castor oil), and mixtures thereof.

Illustrative amphoteric surfactants of the disclosure, e.g., Composition 1.0, et seq., that can be used in the compositions of the invention include betaines (such as cocamidopropylbetaine), derivatives of aliphatic secondary and tertiary amines in which the aliphatic radical can be a straight or branched chain and wherein one of the aliphatic substituents contains about 8-18 carbon atoms and one contains an anionic water-solubilizing group (such as carboxylate, sulfonate, sulfate, phosphate or phosphonate), and mixtures of such materials.

The surfactant or mixtures of compatible surfactants can be present in the compositions of the present invention in 0.1% to 5%, in another embodiment 0.3% to 3% and in another embodiment 0.5% to 2% by weight of the total composition.

Herbal Extracts and Additional Ingredients

Herbal extracts and flavoring agents that can be used in the present disclosure, e.g., Composition 1.0 et seq, include the following: essential oils as well as various flavoring aldehydes, esters, alcohols, and similar materials. Examples of the essential oils include oils of spearmint, peppermint, wintergreen, *sassafras*, clove, sage, *eucalyptus*, marjoram, cinnamon, lemon, lime, grapefruit, and orange. Also useful are such chemicals as menthol, carvone, and anethole. Certain embodiments employ the oils of peppermint and spearmint. The following can also be included in any of the present invention, e.g., any of Composition 1.0 et seq: amla extract, honey extract, almond extract, aloe vera extract, marietta extract, ginger extract, fenugreek, neem seed oil, sesame oil, cinnamon leaf oil, clove oil, thyme oil, *eucalyptus* oil, eugenol, menthol, babool, *Eugenia jambolana* extract (e.g., seed dry extract), *melia azadirachta* (e.g., seed oil), *Gymnema sylvestre*, camphor, and combinations thereof.

Additional ingredients that can be added to the compositions of the disclosure, e.g., any of Composition 1.0 et seq, include: rosemary extract, tea extract, *magnolia* extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, Zinc Chloride, Zinc Lactate, Zinc Sulfate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

Amino Acids

In certain aspects the compositions of the disclosure, e.g., any of Compositions 1.0 et seq, can include a basic or neutral amino acid. The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of 7 or greater.

For example, basic amino acids include, but are not limited to, arginine, lysine, serine, citrullene, ornithine, creatine, histidine, diaminobutanoic acid, diaminoproprionic acid, salts thereof or combinations thereof. In a particular embodiment, the basic amino acids are selected from arginine, citrullene, and ornithine. In certain embodiments, the basic amino acid is arginine, for example, L-arginine, or a salt thereof.

In another aspect, the compositions of the disclosure (e.g., Compositions 1.0 et seq) can include a neutral amino acid, which can include, but are not limited to, one or more neutral amino acids selected from the group consisting of alanine, aminobutyrate, asparagine, cysteine, cystine, glutamine, glycine, hydroxyproline, isoleucine, leucine, methionine, phenylalanine, proline, serine, taurine, threonine, tryptophan, tyrosine, valine, and combinations thereof.

Flavoring Agents

The oral care compositions of the disclosure, e.g., any of Composition 1.0 et seq., may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, *sassafras*, clove, sage, *eucalyptus*, marjoram, cinnamon, lemon, lime, grapefruit, and orange. Also useful are such chemicals as menthol, carvone, and anethole. Certain embodiments employ the oils of peppermint and spearmint.

In one aspect, a flavoring agent is incorporated in the oral composition of the disclosure, e.g., any of Composition 1.0 et seq, at a concentration of 0.01 to 7.5% by weight relative to the total weight of the composition.

pH Adjusting Agents

In some embodiments, the compositions of the present disclosure, e.g., any of Composition 1.0 et seq, contain a buffering agent. Examples of buffering agents include anhydrous carbonates such as sodium carbonate, sesquicarbonates, bicarbonates such as sodium bicarbonate, silicates, bisulfates, phosphates (e.g., monopotassium phosphate, monosodium phosphate, disodium phosphate, dipotassium phosphate, tribasic sodium phosphate, sodium tripolyphosphate, pentapotassium tripolyphosphate, phosphoric acid), citrates (e.g. citric acid, trisodium citrate dehydrate), pyrophosphates (sodium and potassium salts, e.g., tetrapotassium pyrophosphate) and combinations thereof. The amount of buffering agent is sufficient to provide a pH of about 5 to about 9, preferable about 6 to about 8, and more preferable about 7, when the composition is dissolved in water, a mouthrinse base, or a toothpaste base. Typical amounts of buffering agent are about 5% to about 35%, in one embodiment about 10% to about 30%, in another embodiment about 15% to about 25%, by weight of the total composition.

Chelating and Anti-Calculus Agents

The oral care compositions of the disclosure, e.g., any of Composition 1.0 et seq., may include one or more chelating agents able to complex calcium found in the cell walls of the bacteria. Binding of this calcium weakens the bacterial cell wall and augments bacterial lysis.

Another group of agents suitable for use as chelating or anti-calculus agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least 0.1 wt. % pyrophosphate ions, e.g., 0.1 to 3 wt. %, e.g., 0.1 to 2 wt. %, e.g., 0.1 to 1 wt. %, e.g., 0.2 to 0.5 wt %. The pyrophosphates also contribute to preservation of the compositions by lowering water activity.

Suitable anticalculus agents that can be used in oral care compositions of the disclosure (e.g., any of Composition 1.0 et seq) include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. In particular embodiments, the invention includes alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HP O_4$), e.g., in amounts of ca. 3-4% of the sodium phosphate dibasic and ca. 0.2-1% of each of the pyrophosphates. In another embodiment, the compositions comprise a mixture of tetrasodium pyrophosphate (TSPP) and sodium tripolyphosphate (STPP)($Na_5P_3O_{10}$), e.g., in proportions of TSPP at about 1-2% and STPP at about 7% to about 10%. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

Polymers

In one aspect, the oral care compositions of the disclosure, e.g., any of Composition 1.0 et seq., optionally include one or more polymers, such as polyethylene glycols, polyvinyl methyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 1 19 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1 103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

The N-vinyl-2-pyrrolidone is also commonly known as polyvinylpyrrolidone or "PVP". PVP refers to a polymer containing vinylpyrrolidone (also referred to as N-vinylpyrrnlidone and N-vinyl-2-pyrrolidinone) as a monomeric unit. The monomeric unit consists of a polar imide group, four non-polar methylene groups and a non-polar methane group. The polymers include soluble and insoluble homopolymeric PVPs. Copolymers containing PVP include vinylpyrrolidone/vinyl acetate (also known as Copolyvidone, Copolyvidonum or VP-VAc) and vinyl pyrrolidone/ dimethylamino-ethylmethacrylate. Soluble PVP polymers among those useful herein are known in the art, including Povidone, Polyvidone, Polyvidonum, poly(N-vinyl-2-pyrrolidinone), poly (N-vinylbutyrolactam), poly(1-vinyl-2-pyrrolidone) and poly [1-(2-oxo-1 pyrrolidinyl)ethylene]. These PVP polymers are not substantially cross-linked. In some embodiments the polymer comprises an insoluble cross-linked homopolymer. Such polymers include crosslinked PVP (often referred to as cPVP, polyvinylpolypyrrolidone, or cross-povidone).

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, xanthan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

In some embodiments, microcrystalline cellulose (MCC) can be used (e.g., carboxymethyl cellulose with sodium carboxymethyl cellulose). An example of a source of MCC is Avicel® (FMC Corporation), which contains MCC in combination with sodium carboxymethyl cellulose (NaCMC). Both Avicel®. RC-591 (MCC containing 8.3 to 13.8 weight % NaCMC) and Avicel®. CL-611 (MCC containing 11.3 to 18.8 weight % NaCMC) may be used in certain aspects. In certain embodiments, the ratio of microcrystalline cellulose to cellulose ether thickening agent is from 1:1 to 1:3 by weight; or from 1:1.5 to 1:2.75 by weight. In any of the above embodiments comprising sodium carboxymethylcellulose, microcrystalline cellulose may be used in combination with NaCMC. In certain such embodiments, the MCC/sodium carboxymethylcellulose may be present in an amount of from 0.5 to 1.5 weight % based on the total weight of the composition.

Abrasives

Natural calcium carbonate is found in rocks such as chalk, limestone, marble and travertine. It is also the principle component of egg shells and the shells of mollusks. The natural calcium carbonate abrasive of the invention is typically a finely ground limestone which may optionally be refined or partially refined to remove impurities. For use in the present invention, the material has an average particle size of less than 10 microns, e.g., 3-7 microns, e.g., about 5.5 microns. For example, a small particle silica may have an average particle size (D50) of 2.5-4.5 microns. Because natural calcium carbonate may contain a high proportion of relatively large particles of not carefully controlled, which may unacceptably increase the abrasivity, preferably no more than 0.01%, preferably no more than 0.004% by weight of particles would not pass through a 325 mesh. The material has strong crystal structure, and is thus much harder and more abrasive than precipitated calcium carbonate. The tap density for the natural calcium carbonate is for example between 1 and 1.5 g/cc, e.g., about 1.2 for example about 1.19 g/cc. There are different polymorphs of natural calcium carbonate, e.g., calcite, aragonite and vaterite, calcite being preferred for purposes of this invention. An example of a commercially available product suitable for use in the present invention includes Vicron® 25-11 FG from GMZ.

Precipitated calcium carbonate is generally made by calcining limestone, to make calcium oxide (lime), which can then be converted back to calcium carbonate by reaction with carbon dioxide in water. Precipitated calcium carbonate has a different crystal structure from natural calcium carbonate. It is generally more friable and more porous, thus having lower abrasivity and higher water absorption. For use in the oral care compositions of the present disclosure, e.g., any of Composition 1.0 et seq., the particles are small, e.g., having an average particle size of 1-5 microns, and e.g., no more than 0.1%, preferably no more than 0.05% by weight of particles which would not pass through a 325 mesh. The particles may for example have a D50 of 3-6 microns, for example 3.8=4.9, e.g., about 4.3; a D50 of 1-4 microns, e.g., 2.2-2.6 microns, e.g., about 2.4 microns, and a D10 of 1-2 microns, e.g., 1.2-1.4, e.g., about 1.3 microns. The particles have relatively high water absorption, e.g., at least 25 g/100 g, e.g., 30-70 g/100 g. Examples of commercially available products suitable for use in the present invention include, for example, Carbolag® 15 Plus from Lagos Industria Quimica.

In certain embodiments the oral care compositions of the present disclosure, e.g., any of Composition 1.0 et seq., may comprise additional calcium-containing abrasives, for example calcium phosphate abrasive, e.g., tricalcium phosphate $(Ca_3(PO4)_2)$, hydroxyapatite $(Ca_{10}(PO4)_6(OH)_2)$, or dicalcium phosphate dihydrate $(CaHP O_4 \cdot 2H_2O$, also sometimes referred to herein as DiCal) or calcium pyrophosphate, and/or silica abrasives, sodium metaphosphate, potassium metaphosphate, aluminum silicate, calcined alumina, bentonite or other siliceous materials, or combinations thereof. Any silica suitable for oral care compositions may be used, such as precipitated silicas or silica gels. For example synthetic amorphous silica. Silica may also be available as a thickening agent, e.g., particle silica. For example, the silica can also be small particle silica (e.g., Sorbosil AC43 from PQ Corporation, Warrington, United Kingdom). However the additional abrasives are preferably not present in a type or amount so as to increase the RDA of the dentifrice to levels which could damage sensitive teeth, e.g., greater than 130.

Water

Water is present in the oral compositions of the present disclosure. Water, employed in the preparation of commercial oral compositions should be deionized and free of organic impurities. Water commonly makes up the balance of the compositions and includes, e.g., 5% to 45%, e.g., 10% to 20%, e.g., 25-35%, by weight of the oral compositions. This amount of water includes the free water which is added plus that amount which is introduced with other materials such as with sorbitol or silica or any components of the invention. The Karl Fischer method is a one measure of calculating free water.

Humectants

Within certain embodiments of the oral compositions of the disclosure, e.g., any of Composition 1.0 et seq, it is also desirable to incorporate a humectant to reduce evaporation and also contribute towards preservation by lowering water activity. Certain humectants can also impart desirable sweetness or flavor to the compositions. The humectant, on a pure humectant basis, generally includes 15% to 70% in one embodiment or 30% to 65% in another embodiment by weight of the composition.

Suitable humectants include edible polyhydric alcohols such as glycerin, sorbitol, xylitol, propylene glycol as well as other polyols and mixtures of these humectants. Mixtures of glycerin and sorbitol may be used in certain embodiments as the humectant component of the compositions herein.

The present invention in its method aspect involves applying to the oral cavity a safe and effective amount of the compositions described herein.

The compositions and methods according to the disclosure (e.g., any of Composition 1.0 et seq) can be incorporated into oral compositions for the care of the mouth and teeth such as dentifrices, toothpastes, transparent pastes, gels, mouth rinses, sprays and chewing gum. The compositions and methods according to the disclosure (e.g., any of Composition 1.0 et seq) can be incorporated into oil-pulling formats as well.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1

Representative Formulas (Values are % Wt. Of the Composition)

TABLE A

| Description | Weight % |
| --- | --- |
| Humectant (70% Solution) | 30.0 |
| Flavor and sweetener | 2.05 |
| Sodium Monofluorophosphate | 0.76 |
| Sodium Carboxymethyl Cellulose | 0.7 |
| pH Adjusting Agent | 0.5 |
| Purified Water | q.s. (e.g., 11%-15%) |
| Thickener | 1.5 |
| Precipitated Calcium Carbonate | 40.0 |

TABLE A-continued

| Description | Weight % |
|---|---|
| Anionic Surfactant | 1.9 |
| Zinc Oxide | 1.0 |
| Zinc Citrate | 0.5 |
| Stabilizing agent | 0.3 |
| Sodium silicate | 1.0 |
| Preservative | 0.3 |
| Amla extract | 0.1 |
| *Gymnema sylvestre* Extract | 0.3 |
| *MELIA AZADIRACHTA* seed oil | 0.01 |
| *Eugenia jambolana* Seed Dry Extract | 0.0004 |
| Alkali phosphate salt | 0.5 |
| Total Components | 100 |

Example 2

IL-1β Mediated PGE2 Suppression with *Gymnema sylvestre* Treatment (Tissue Model)

PGE2, a marker of inflammation, can be increased via administration of IL-1β. Samples are subjected to the Matek Gingival Tissue Model. Untreated samples are compared to samples treated with IL-1β (only) and samples with IL-1β and *Gymnema sylvestre* 0.3% by wt. As demonstrated in Table B below, samples treated with both IL-1β and *Gymnema sylvestre* demonstrated PGE2 values that are similar to samples are untreated. This finding demonstrates that at 0.3% by wt. that samples with *Gymnema sylvestre* can suppress IL-1β mediated inflammation in vitro.

TABLE B

| Sample | PGE2 (ng/ml) |
|---|---|
| Untreated (positive control) | 430.7 |
| Tissues treated with IL-1 β | 1008.9 |
| Tissues treated with IL-1 β and 0.3% *Gymnema sylvestre* extract | 420.5 |

IL-1β Mediated PGE2 Suppression with *Gymnema sylvestre* Treatment (Oral Gingival Model)

PGE2, a marker of inflammation, can be increased via administration of IL-1β. The effect of tissue contacted with toothpaste samples is assessed in the oral gingival model. Untreated tissue samples are compared to samples treated with IL-1β (only) and samples with IL-1β and *Gymnema sylvestre* 0.3% by wt. As demonstrated in Table C below, samples treated with both IL-1β and *Gymnema sylvestre* demonstrates PGE2 values that are similar to samples are untreated. This finding demonstrates that at 0.3% by wt. that samples with *Gymnema sylvestre* can suppress IL-1β mediated inflammation in vitro. In this assay, placebo (untreated) and gurmar containing toothpaste slurry are prepared in water and applied topically on in-vitro gingival tissues for 2 minutes and subsequently rinsed with PBS. Tissues are subjected to overnight treatment with medium containing IL-1beta at 37 degrees in the tissue culture incubator. Cell Culture Supernatants are Evaluated for PGE2 Levels by ELISA.

TABLE C

| Sample | PGE2 (ng/ml) |
|---|---|
| Untreated (positive control) | 430.7 |
| Tissues treated with IL-1 β | 580.4 |

TABLE C-continued

| Sample | PGE2 (ng/ml) |
|---|---|
| Tissues treated with IL-1 β and 0.3% *Gymnema sylvestre* toothpaste | 328.7 |

IL-1β Mediated PGE2 Suppression with *Gymnema sylvestre* Treatment (Cell Model)

PGE2, a marker of inflammation, can be increased via administration of IL-1β. Samples are subjected to the HEPM monolayer cell model assay. Healthy cells (not treated with IL-1β) are compared to inflamed cells (samples treated with IL-1β (only)), samples treated with a positive control (Triclosan), samples with IL-1β and *Gymnema sylvestre* 0.039% by wt. (390 ppm), and samples with IL-1β and *Gymnema sylvestre* 0.0195% by wt. (195 ppm). As demonstrated in Table D below, samples treated with both IL-1β and *Gymnema sylvestre* demonstrate PGE2 values, at 0.039% and 0.0195% treatments, are approximately 20% and 30% lower, respectively, relative to inflamed cells treated with only IL-1β. This finding demonstrates that at 0.039% by wt., and 0.0195% by wt., that samples with *Gymnema sylvestre* are believed to suppress IL-1β mediated inflammation in vitro.

TABLE D

| Sample | PGE2 (pg/ml) |
|---|---|
| Healthy cells (untreated, positive control) | 446.0 |
| Inflamed cells (treated with only IL-1 β) | 1909.9 |
| Cells treated with IL-1 β and Triclosan (0.001%) | 520.9 |
| Cells treated with IL-1 β and Triclosan (0.0005%) | 715.9 |
| Cells treated with IL-1 β and 0.039% (390 ppm) *Gymnema sylvestre* extract | 1177.3 |
| Cells treated with IL-1 β and 0.0195% (195 ppm) *Gymnema sylvestre* extract | 1483.7 |
| Cells treated with IL-1 β and 0.391% DMSO | 1759.0 |

Example 3

A three-month gingival bleeding study is conducted. Test Formula A (described below) is used and compared to a control formulation. The criteria used for the "Gingival Index" and "Plaque Index" scores are according to the Loe-Silness measurement scale which is available to one of skill in the art. See, Silness J, Löe H. Periodontal disease in pregnancy ii. Correlation between oral hygiene and periodontal condition. *Acta Odontol Scand.* 1964; 22:121-135, the contents of which are incorporated herein by reference.

The results are as follows and demonstrate the percent reductions between treatments relative to the control:

TABLE E

| Gingival Index (Loe-Silness) Between-Treatment Reductions | |
|---|---|
| Index | Percent Difference (Relative to control) |
| Gingival (Whole Mouth) | 21.9%* |
| Gingival Severity (Gum Bleeding) | 51.5%* |

TABLE E-continued

| Gingival Index (Loe-Silness) Between-Treatment Reductions | |
|---|---|
| Index | Percent Difference (Relative to control) |
| Gingival Interproximal (In-between teeth) | 22.5%* |

TABLE F

| Ayurveda (Visual Analog Scale) Between-Treatment Reductions | |
|---|---|
| Index | Percent Difference (Relative to control) |
| Shotha (Inflammation) | 34.5%* |
| Rakatasrava (Gum Bleeding) | 29.7%* |
| Dantamamsa mriduta (Sponginess of Gums) | 38.0%* |

*Indicates statistical significance relative to control

The test formula here is a fluoride ayurvedic toothpaste of "Test Formula A", as detailed in the below table, containing zinc and gurmar in a chalk base and provides a significantly greater reduction in gingival bleeding as compared to a commercially available fluoride toothpaste (as detailed in the below table) after 12 weeks of product use.

Additionally, after six months of product use, with the same Test and Control formulas, the results are as follows:

TABLE G

| Gingival Index (Loe-Silness) (Six month results) Between-Treatment Reductions | |
|---|---|
| Index | Percent Difference (Relative to control) |
| Gingival (Whole Mouth) | 14.0%* |
| Gingival Severity (Gum Bleeding) | 32.9%* |
| Gingival Interproximal (In-between teeth) | 14.8%* |

TABLE H

| Plaque Index (Loe-Silness) (Six-month results) Between-Treatment Reductions | |
|---|---|
| Index | Percent Difference (Relative to control) |
| Gingival (Whole Mouth) | 7.6%* |
| Gingival Severity (Gum Bleeding) | 21.9%* |
| Gingival Interproximal (In-between teeth) | 7.2%* |

TABLE I

| Ayurveda (Visual Analog Scale) (Six-month results) Between-Treatment Reductions | |
|---|---|
| Index | Percent Difference (Relative to control) |
| Shotha (Inflammation) | 35.7%* |
| Rakatasrava (Gum Bleeding) | 38.7%* |
| Dantamamsa mriduta (Sponginess of Gums) | 41.6%* |

*Indicates statistical significance relative to control

Accordingly, an ayurvedic fluoride toothpaste containing zinc salts, gurmar in a calcium carbonate base provides a significantly greater reduction in dental plaque and gingivitis as compared to a commercially available fluoride toothpaste after 6 months of product use.

The Control and Test Formula Toothpaste used in this clinical trial are as follows:

Control Toothpaste Formula is a toothpaste as follows:

| Ingredient | Weight % |
|---|---|
| Humectant | 18.0 |
| Thickening agent | — |
| Sodium Monofluorophosphate | 0.76 |
| Sodium Bicarbonate | 0.50 |
| Purified Water | q.s. |
| Thickener Silica | 1.0 |
| Calcium Carbonate | 48.0 |
| Anionic surfactant | 2.20 |
| Zinc Oxide | — |
| Zinc Citrate | — |
| Potassium Nitrate | 0.50 |
| Sodium Silicate | 1.13 |
| Benzyl Alcohol | 0.3 |
| Flavor, Sweetener, Color | 1.2 |
| Sodium Carboxymethyl Cellulose | 1.0 |
| Amla Extract | — |
| *Gymnema Sylvestre* Extract | — |
| *Eugenia jambolana* Seed Dry Extract | — |
| *MELIA AZADIRACHTA* seed oil | — |
| Total Components | 100.0 |

"Test Formula A" is a toothpaste as follows:

| Ingredient | Weight % |
|---|---|
| Humectant | 30.0 |
| Thickening agent | 0.825 |
| Sodium Monofluorophosphate | 0.76 |
| Sodium Bicarbonate | 0.5 |
| Purified Water | q.s. |
| Thickener Silica | 1.75 |
| Calcium Carbonate | 40.5 |
| Anionic surfactant (e.g., 95% anionic surfactant granules) | 2.0 |
| Zinc Oxide | 1.0 |
| Zinc Citrate | 0.50 |
| Potassium Nitrate | 0.30 |
| Sodium Silicate | 1.0 |
| Benzyl Alcohol | 0.3 |
| Amla Extract | 0.1 |
| *Gymnema Sylvestre* Extract | 0.3 |
| *Eugenia jambolana* Seed Dry Extract | 0.0004 |
| *MELIA AZADIRACHTA* seed oil | 0.01 |
| Total Components | 100.0 |

Example 4

The following are representative formulas of the present invention:

| Ingredient | Weight % | Weight % | Weight % | Weight % |
|---|---|---|---|---|
| Sorbitol (70% solution) | 30 | 30 | 30 | 30 |
| Carrageenan | 0.825 | 0.825 | 0.825 | — |
| Sodium Monofluorophosphate | 0.76 | 0.76 | 0.76 | 0.76 |
| pH Adjusting Agent | 0.5 | 0.5 | 0.5 | 0.5 |
| Purified Water | q.s. | q.s | q.s | q.s |
| Thickener Silica | 1.75 | 1.75 | 1.75 | 2.0 |
| Natural Calcium Carbonate | 19.0 | 19.0 | 19.0 | — |
| Precipitated Calcium Carbonate | 21.5 | 21.5 | 21.5 | 46.0 |
| Anionic Surfactant | 2.0 | 2.0 | 2.0 | 2.0 |
| Zinc Oxide | 1.00 | 1.00 | 1.00 | 1.00 |
| Zinc Citrate Trihydrate | 0.50 | 0.50 | 0.50 | 0.50 |
| Stabilizing agent | 0.3 | 0.3 | 0.3 | 0.3 |
| Sodium Silicate | 1.0 | 1.0 | 1.0 | 1.0 |
| Preservative agent | 0.3 | 0.3 | 0.3 | 0.3 |
| Alkali Phosphate Salt | | | | 0.5 |
| Sodium Carboxymethyl Cellulose | | | | 0.7 |
| Flavor, Color, Sweetener | 1.0 | 1.85 | 1.7 | 5.25 |
| Amla Extract | 0.1 | 0.1 | 0.1 | 0.1 |
| *Gymnema Sylvestre* Extract | 0.3 | 0.3 | 0.3 | 0.3 |
| *Eugenia jambolana* Seed Dry Extract | 0.0004 | 0.0004 | 0.0004 | 0.0004 |
| *MELIA AZADIRACHTA* seed oil | 0.01 | 0.01 | 0.01 | 0.01 |
| Additional Natural Extracts and Oils | | | | 0.002 |
| Total Components | 100.0 | 100.0 | 100.0 | 100.0 |

Example 5

Toothpastes of the present invention are tested for antibacterial efficacy.

For this efficacy evaluation, the University of Manchester (UoM) anaerobic biofilm Growth Inhibition model is used to indicate potential performance of formulas against anaerobic biofilm. Anaerobic biofilms are usually the disease causing organisms (difficult to kill). In this method, the biofilm are grown in a zero oxygen environment on the Hydroxyapatite discs (HAP). Without being bound by theory, this method is close to clinical study due to use of human saliva as inoculum and the duration of the study which is ten days long.

The anaerobic model (UoM) is used to provide a more sensitive indication of potential efficacy of the formula. In this model, saliva collected from four healthy volunteers and pooled together are used as an inoculum. The discs are immersed in the mixture of human saliva & artificial saliva in a proportion of 1:1. The discs are incubated for 24 hrs allowing biofilm to develop. The discs are treated with toothpaste 1:2 slurry in water. Each sample is treated in triplicate twice a day for 8 days. Recovery and quantification of biofilms on HAP is done on day 10. The anaerobic chamber does not allow the growth of aerobes. In this study, we have recovered the biofilm after 16 treatments to measure ATP (RLU) (Promega BactitreGlo Microbial Cell Viability kit) as an end point for viable bacteria.

Formula B, Formula C, and Formula D are tested in this model and compared against two negative controls and a positive control. The positive control comprises stannous fluoride, zinc oxide, zinc citrate, and stannous pyrophosphate. Negative Control #1 is a market-based toothpaste with a fluoride source, but which does not contain zinc citrate, zinc oxide, or the herbal extracts listed in Formulas B, C, or D. Negative Control #2 is the same formula as the "Control Toothpaste Formula" referenced in Example 3 above. The results of the study are as follows:

| SAMPLE | Log RLU |
|---|---|
| Negative Control # 1 | 5.37 |
| Negative Control # 2 | 4.16 |
| Formula B | 4.05 |
| Formula C | 3.91 |
| Formula D | 3.91 |
| Positive Control | 3.86 |

Antibacterial Efficacy Study (University of Manchester Model)

Formulas B, C, and D all demonstrate acceptable antibacterial efficacy as compared to both controls. The ingredients for Formulas B, C, and D are listed in Table L below.

TABLE L

| Ingredient | Formula B (% wt.) | Formula C (% wt.) | Formula D (% wt.) |
|---|---|---|---|
| PRECIPITATED CALCIUM CARBONATE | 21.50 | 21.50 | 40.00 |
| REFINED NATURAL CALCIUM CARBONATE | 19.00 | 19.00 | — |
| SORBITOL - 70% SOLUTION | 30.00 | 30.00 | 30.00 |
| SODIUM LAURYL SULFATE (GRANULES) | 2.00 | 2.00 | 6.5517 |
| PURIFIED WATER | 19.1546 | 18.1046 | 13.9279 |
| THICKENER | 1.75 | 1.75 | 1.50 |
| SODIUM SILICATE LIQUID | 1.00 | 1.00 | 1.00 |
| ZINC OXIDE | 1.00 | 1.00 | 1.00 |
| SODIUM MONOFLUOROPHOSPHATE | 0.76 | 0.76 | 0.76 |
| SODIUM CARBOXYMETHYL CELLULOSE | — | — | 0.70 |
| CARRAGEENAN | 0.825 | 0.825 | — |
| pH ADJUSTING AGENT | 0.50 | 0.50 | 0.50 |
| ZINC CITRATE TRIHYDRATE | 0.50 | 0.50 | 0.50 |
| ALKALI PHOSPHATE SALT | — | — | 0.50 |
| POTASSIUM NITRATE | 0.30 | 0.30 | 0.30 |
| PRESERVATIVE | 0.30 | 0.30 | 0.30 |
| AMLA EXTRACT | 0.10 | 0.10 | 0.10 |
| NEEM (*MELIA AZADIRACHTA*) SEED OIL | 0.01 | 0.01 | 0.01 |
| FLAVOR, SWEETENER | 1.00 | 2.05 | 2.05 |
| GUDMAR (*GYMNEMA SYLVESTRE*) DRY EXTRACT | 0.30 | 0.30 | 0.30 |
| JAMBU (*EUGENIA JAMBOLANA*) SEED DRY EXTRACT | 0.0004 | 0.0004 | 0.0004 |
| Total | 100.000 | 100.000 | 100.000 |

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

While the present invention has been described with reference to embodiments, it will be understood by those skilled in the art that various modifications and variations may be made therein without departing from the scope of the present invention as defined by the appended claims.

The invention claimed is:

1. An oral care composition comprising:
   a. an effective amount of a zinc ion source;
   b. a fluoride source; and
   c. an herbal extract consisting of:
      from 0.1 to less than 0.5 wt. % of *Gymnema sylvestre* extract, based on the weight of the oral care composition, and *Eugenia jambolana* extract, and optionally *melia azadirachta* seed oil and/or amla extract, wherein the oral care composition is free of herbal extracts other than *Gymnema sylvestre* extract, *Eugenia jambolana* extract, *melia azadirachta* seed oil and amla extract, and wherein
      the oral care composition demonstrates at least a 35% reduction in gum sponginess, relative to a control that does not contain the zinc ion source and the herbal extract, wherein the reduction is measured by a Visual Analog Scale.

2. The oral care composition of claim 1, wherein the zinc ion source comprises zinc citrate and zinc oxide, where the wt. % ratio of the amount of zinc oxide to zinc citrate is from 1.5:1 to 4.5:1.

3. The oral care composition of claim 1, wherein the zinc ion source comprises zinc citrate and zinc oxide, wherein the zinc citrate is present in an amount of from 0.25 to 1 wt. % and zinc oxide is present in an amount of from 0.75 to 1.25 wt. %, based on the weight of the oral care composition.

4. The oral care composition of claim 1 wherein the fluoride source is selected from: stannous fluoride, sodium fluoride, potassium fluoride, sodium monofluorophosphate, sodium fluorosilicate, ammonium fluorosilicate, amine fluoride, ammonium fluoride, titanium fluoride, hexafluorosulfate, or combinations thereof.

5. The oral care composition of claim 4, wherein the fluoride source is sodium monofluorophosphate.

6. The oral care composition of claim 1 wherein the herbal extract includes amla extract.

7. The oral care composition of claim 6 wherein the oral care composition includes *melia azadirachta* seed oil.

8. The oral care composition of claim 1, wherein the composition comprises:
   a. from 0.5 to 1.5 wt. % zinc oxide;
   b. from 0.25 to 0.75 wt. % zinc citrate;
   c. from 0.5 to 1.0 wt. % of sodium monofluorophosphate; and d. from 0.2 to 0.5 wt. % of a combination of *Gymnema sylvestre* extract, *Eugenia jambolana* extract, *melia azadirachta* seed oil, and amla extract, wherein all weight percentages are based on the total weight of the oral care composition.

9. The oral care composition of claim 1, wherein the composition comprises:
   a. from 0.5 to 1.5 wt. % of zinc oxide;
   b. from 0.25 to 0.75 wt. % of zinc citrate;
   c. from 0.5 to 1.0 wt. % of sodium monofluorophosphate; and
   d. an herbal extract consisting of: from 0.2 to 0.5 wt. % of *Gymnema sylvestre* extract, and *Eugenia jambolana* extract,
      wherein all weight percentages are based on the total weight of the oral care composition.

10. The oral care composition of claim 1, wherein the oral care composition is in a form selected from: a toothpaste, transparent paste, gel, mouth rinse, spray or chewing gum.

11. The oral care composition of claim 1, wherein the oral care composition demonstrates at least a 50% reduction in gum bleeding, relative to the control, wherein the reduction is measured by the Loe-Silness Gingival Index.

12. The oral care composition of claim 1, wherein the oral care composition demonstrates at least a 25% reduction in gum bleeding, relative to the control, wherein the reduction is measured by a Visual Analog Scale.

13. The oral care composition of claim 1, wherein the oral care composition is administered in an amount effective to reduce IL-1β mediated inflammation.

14. A method for treating or reducing gingivitis in a subject in need thereof, wherein the method comprises administering an oral care composition of claim 1 to the subject in need thereof.

15. The method of claim 14, wherein the subject is at risk because the subject is diabetic or has been diagnosed with diabetes.

16. An oral care composition comprising:
   a zinc source;
   a fluoride source;
   from 20 to 50 wt. % of a calcium carbonate;
   water; and
   an herbal extract present in a total amount of 0.2 to 0.5 wt. %, the herbal extract consisting of *Gymnema sylvestre* extract and amla extract, wherein the oral care composition is free of herbal extracts other than *Gymnema sylvestre* extract and amla extract, and wherein
   all weight percentages are based on the total weight of the oral care composition.

* * * * *